(12) United States Patent
Uotani et al.

(10) Patent No.: US 7,910,089 B2
(45) Date of Patent: Mar. 22, 2011

(54) SIALOGOGUE, ORAL COMPOSITION AND FOOD PRODUCT CONTAINING THE SAME

(75) Inventors: Kazumichi Uotani, Tokyo (JP); Hidetoshi Kubota, Sakado (JP); Hiroya Endou, Sakado (JP); Fumihiko Tokita, Tokyo (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 636 days.

(21) Appl. No.: 10/579,731

(22) PCT Filed: Nov. 16, 2004

(86) PCT No.: PCT/JP2004/017328
§ 371 (c)(1),
(2), (4) Date: May 17, 2006

(87) PCT Pub. No.: WO2005/049050
PCT Pub. Date: Jun. 2, 2005

(65) Prior Publication Data
US 2007/0099827 A1 May 3, 2007

(30) Foreign Application Priority Data
Nov. 19, 2003 (JP) .................................. 2003-388809

(51) Int. Cl.
*A61K 8/66* (2006.01)
*A61K 8/96* (2006.01)
*A61K 38/00* (2006.01)
*A61K 51/00* (2006.01)

(52) U.S. Cl. ............ 424/50; 514/1.1; 530/300; 424/1.69

(58) Field of Classification Search .................... None
See application file for complete search history.

(56) References Cited

U.S. PATENT DOCUMENTS

| | | | |
|---|---|---|---|
| 4,232,007 A | 11/1980 | Kajihara et al. | |
| 5,447,732 A * | 9/1995 | Tanimoto et al. | 426/74 |
| 5,496,558 A * | 3/1996 | Napolitano et al. | 424/435 |
| 6,350,438 B1 | 2/2002 | Witt et al. | |
| 2003/0003061 A1 | 1/2003 | Yue et al. | |
| 2003/0017209 A1 * | 1/2003 | Parikh et al. | 514/23 |
| 2003/0039706 A1 | 2/2003 | Hirose et al. | |
| 2003/0195160 A1 * | 10/2003 | Johnson | 514/23 |
| 2003/0199456 A1 * | 10/2003 | Johnson | 514/23 |
| 2004/0013723 A1 * | 1/2004 | Parikh et al. | 424/456 |
| 2004/0063612 A1 * | 4/2004 | Yalpani | 514/2 |

FOREIGN PATENT DOCUMENTS

| | | |
|---|---|---|
| CN | 95196906 A | 1/1998 |
| EP | 0 613 684 A1 | 9/1994 |
| JP | 56-22719 A | 3/1981 |
| JP | 59209635 * | 11/1984 |
| JP | 03047087 A | 2/1991 |
| JP | 05304977 A | 11/1993 |
| JP | 7-101856 A | 4/1995 |
| JP | 08112084 A | 5/1996 |
| JP | 10-182392 A | 7/1998 |
| JP | 10-511351 A | 11/1998 |
| JP | 10298058 A | 11/1998 |
| JP | 2002-265375 A | 9/2002 |
| JP | 2003-526649 A | 9/2003 |
| JP | 2004-91404 A | 3/2004 |
| JP | 2006083100 A | 3/2006 |
| JP | 2007326808 A | 12/2007 |
| WO | WO-96/19193 A1 | 6/1996 |
| WO | WO-00/56344 A1 | 9/2000 |
| WO | WO-01/54657 A1 | 8/2001 |
| WO | WO-01/68046 A2 | 9/2001 |
| WO | WO-02/02061 A2 | 1/2002 |

OTHER PUBLICATIONS

Anonymous; "Utilisation de Polyaminoacides en Hygiene Bucco-Dentaire"; Research Disclosure, Mason Publications, vol. 353, No. 21, Sep. 1, 1993.
Uotani Kazumichi; "Poly(glutamic acid) and sialagogic action"; Chemicals Abstracts Service; Feb. 25, 2005; Database accession No. 2005:161170.

\* cited by examiner

*Primary Examiner* — Maury Audet
(74) *Attorney, Agent, or Firm* — Birch, Stewart, Kolasch & Birch, LLP

(57) ABSTRACT

A sialogogue characterized by comprising polyglutamic acid or its salt. This sialogogue is blended into an oral composition and a food product. This sialogogue is capable of rendering the oral mucosa pleasant even in the case of severe xerostomia.

10 Claims, 2 Drawing Sheets

SIALOGOGUE, ORAL COMPOSITION AND FOOD PRODUCT CONTAINING THE SAME

This application claims priority under 35 U.S.C. §371 on PCT International Application No. PCT/JP2004/017328 filed on 16 Nov. 2004, the entire contents of which are hereby incorporated by reference.

TECHNICAL FIELD

The present invention relates to a sialogogue for curing mouth dryness and an oral composition and food product incorporated therewith.

BACKGROUND ART

Xerostomia (dry mouth) is a physiological phenomenon which is experienced in daily life. It gives sticky displeasure, makes speaking difficult, and causes bad breath. In its pathological state, it changes the oral microbial flora, thereby creating a failure in oral functions such as dental caries, periodontal disease, and mucosal infectious disease. Consequently, promoting salivary secretion and thereby wetting the oral cavity are important in making the oral cavity feel refreshed and preventing oral diseases.

So, it has been recognized that wetting the oral cavity is necessary to make the oral cavity feel refreshed and prevent oral diseases. To meet this requirement, there has been proposed the use of hyaluronic acid (which is a humectant) in WO00/56344. There has also been proposed an idea of positively promoting salivary secretion, thereby wetting the oral cavity. To materialize this idea, there has been proposed the use of a sialogogue selected from pickled Japanese apricot or Japanese apricot vinegar (in Japanese Patent Laid-Open No. Sho 56-22719) or organic acid (in Japanese Patent Laid-Open No. Hei 7-101856). There have also been proposed other sialogogues which do not resort to acid stimulation. Japanese Patent Laid-Open No. Hei 10-182392 discloses Cola nuts (Sterculiaceae) and Japanese Patent Laid-Open No. 2002-265375 discloses Capparis masaikai (Capparidaceae), Capparis pterocarpa Chun (Capparidaceae) and Centella asiatica (Umbelliferae).

Regrettably, hyaluronic acid produces the moisturizing effect but does not positively promote salivary secretion. Moreover, the above-mentioned sialogogues are limited in their use because they taste somewhat.

DISCLOSURE OF INVENTION

It is an object of the present invention to provide a sialogogue and an oral composition and food product incorporated therewith. The sialogogue is tasteless and capable of moisture retention. The oral composition incorporated with the sialogogue includes toothpaste, mouthwash, artificial saliva, denture stabilizer, and solution for the oral care system with water supply and suction functions. The food product includes swallowing assistant, chewing gum, candy, drinks, and gummi.

In order to achieve the above-mentioned object, the present inventors carried out a series of researches, which led to the finding that polyglutamic acid and salts thereof promote salivary secretion and produce moisturizing effect and are almost tasteless and hence capable of incorporation into oral compositions and food products without the possibility of impairing their taste. The present invention is based on this finding.

Thus, the present invention is directed to a sialogogue including polyglutamic acid or a salt thereof and also to an oral composition and a food product both incorporated with the sialogogue.

The sialogogue according to the present invention moisturizes the oral mucous membrane of a patient suffering from serious dry mouth. Therefore, it easily solves problems with sticky displeasure, difficulties in speaking, and bad breath. In addition, it also prevents a failure in oral functions, such as dental caries, periodontal disease, and mucosal infectious disease. Being almost tasteless, it can be incorporated into oral compositions and food products without restrictions. Moreover, being known as the sticking component of natto (fermented soybeans), it is highly safe and suitable for oral compositions and food products.

BEST MODE FOR CARRYING OUT THE INVENTION

Figure 1:
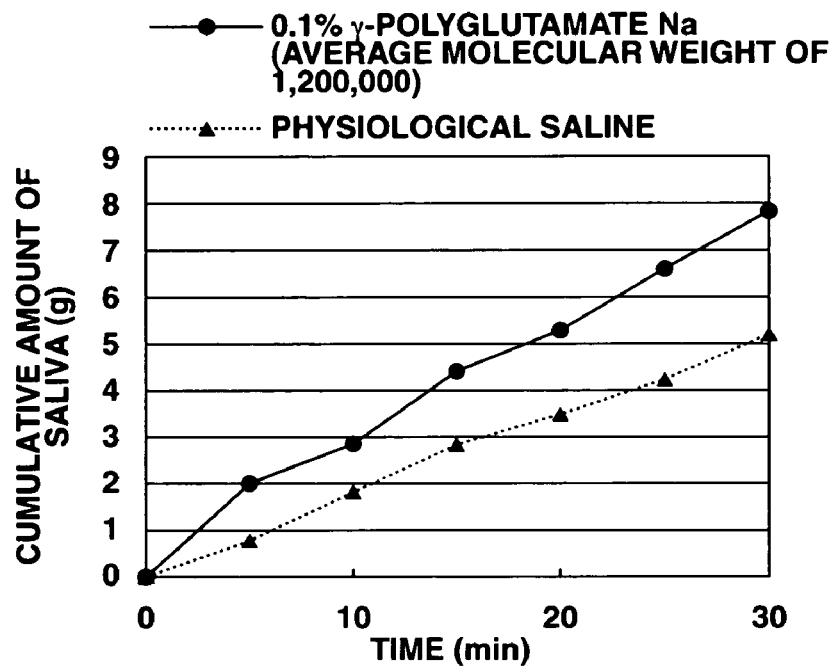
FIG. 1 is a graph showing how the cumulative amount of saliva changes with time after administration of sodium γ-polyglutamate (with an average molecular weight of 1,200,000) in Experiment Example 1.

The sialogogue according to the present invention is polyglutamic acid, which is chemically synthesized α- or γ-polyglutamic acid or a salt thereof, or natural α- or γ-polyglutamic acid or a salt thereof obtained from a variety of strains as a product of fermentation. Natural polyglutamic acid is desirable for incorporation into oral compositions and food products. Most desirable is γ-polyglutamic acid which is industrially available in large quantities. The polyglutamic acid may be either of D-form or L-form. The polyglutamic acid is insoluble in water but its salt is soluble in water. The salt includes sodium salt, potassium salt, magnesium salt, calcium salt, ammonium salt, ethanolamine salt, and basic amino acid salt. Any salt may be used which is suitable for oral compositions and food products. The polyglutamic acid may be neutralized to an adequate degree which is known from the fact that a 1 wt % aqueous solution of the polyglutamate marks pH 1 to pH 14. The polyglutamic acid used in the present invention is not specifically restricted in molecular weight. However, the weight average molecular weight (in terms of sodium salt measured by the method mentioned later) should be 10,000 to 5,000,000, preferably 20,000 to 4,000,000, more preferably 40,000 to 3,000,000, and most preferably 50,000 to 2,000,000. An adequate molecular weight should be selected according to the type of the product.

Sodium polyglutamate represented by the formula (1) below is particularly desirable.

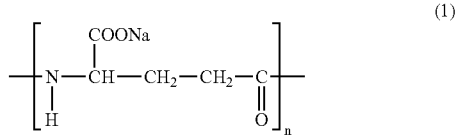

(wherein n is an integer of 66 to 33,112, especially 331 to 13,245.)

The polyglutamic acid or a salt thereof to be used as the sialogogue according to the present invention should be added to oral compositions or food products in an amount of 0.001 to 10% by weight, preferably 0.005 to 7% by weight, more preferably 0.01 to 5% by weight, and most desirably 0.05 to 3% by weight. An amount less than the lower limit will not produce the desired effect, and an amount more than the upper limit will increase viscosity to adversely affect the feeling.

The sialogogue according to the present invention may be administered 1 to 6 times a day, with each dose ranging from 0.01 to 1 g, which is enough to promote salivary secretion.

The sialogogue according to the present invention may be incorporated into oral compositions and food product. The oral compositions include toothpaste, mouthwash, chewing tablet, oral ointment, gargling tablet, troches, artificial saliva, denture stabilizer, and solution for the oral care system with water supply and suction functions. The food product includes swallowing assistant, candy, chewing gum, drinks, and gummi. The sialogogue may be used in combination with any known component according to the kind and form of the oral composition and food product.

Those components used for oral compositions in the form of liquid or paste include humectant, binder, surfactant, sweetener, antiseptic, colorant, flavor, and other effective ingredients. They may be mixed with water to produce the desired products. Another component used for toothpaste is an abrasive.

The humectant is exemplified by polyhydric alcohols such as sorbitol, glycerin, propylene glycol, polyethylene glycol, xylitol, multitol, and lactitol. Its amount should be 5 to 50% by weight, particularly 20 to 45% by weight for paste products, and 0 to 50% by weight, particularly 1 to 20% by weight for liquid products.

The binder is exemplified by carrageenan, sodium hydroxyethyl cellulose, sodium carboxymethyl cellulose, hydroxyethyl cellulose, hydroxypropyl cellulose, methyl cellulose, hydroxypropylmehtyl cellulose, sodium alginate, propylene glycol ester of alginic acid, polyacrylic acid, sodium polyacrylate, xanthan gum, talha gum, guar gum, locust bean gum, jellan gum, gelatin, curdlan, gum Arabic, agar, pectin, polyvinyl alcohol, polyvinyl pyrrolidone, and pullulan. The amount of the binder ranges from 0.1 to 5% by weight for paste products (such as toothpaste) and 0 to 5% by weight for liquid products (such as liquid dentifrice and mouthwash).

The surfactant is exemplified by anionic surfactant, cationic surfactant, and nonionic surfactant. Their typical examples include sodium lauryl sulfate, sodium α-olefinsulfonate, N-acylglutamate, 2-alkyl-N-carboxylmethyl-N-hydroxyethylimidazolinium betaine, N-acyltaurate, sugar fatty acid ester, alkylolamide, polyoxyethylene hardened castor oil, polyglycerin fatty acid ester, polyoxyethylene-polyoxypropylene glycol, polyoxyethylenesorbitan monostearate, lauroylsarcosine sodium, alkylpolyglucoside, and polyoxyethylene alkyl ether sulfosuccinate. The amount of the surfactant is usually 0.5 to 5% by weight.

The sweetener is exemplified by saccharine sodium, stevioside, stevia extract, paramethoxycinnamic aldehyde, neohesperidyl hydrochalcone, and perillartine. The colorant is exemplified by Blue No. 1, Yellow No. 4, and titanium dioxide. The antiseptic is exemplified by parahydroxybenzoate ester and sodium benzoate.

The flavor is exemplified by terpenes and their derivatives (such as 1-menthol, carvone, anethole, and limonene) and peppermint oil.

The liquid agents may be incorporated with a nontoxic solvent (such as ethanol) in an amount of 0 to 30% by weight, particularly 1 to 25% by weight.

The abrasive is exemplified by silica gel, precipitated silica, aluminosilicate, zirconosilicate, dibasic calcium phosphate anhydride or dihydrate, calcium pyrophosphate, calcium tertiary phosphate, hydroxyapatite, calcium carbonate, aluminum hydroxide, alumina, magnesium carbonate, magnesium tertiary phosphate, zeolite, zirconium silicate, and plastic-based abrasive.

The preferred amount of the abrasive ranges from 10 to 50% by weight for toothpaste and 0 to 30% by weight for liquid dentifrice.

The artificial saliva may be incorporated with potassium chloride (0.1 to 0.2% by weight), sodium chloride (0.05 to 0.1% by weight), calcium chloride (0.01 to 0.02% by weight), and magnesium chloride (0.004 to 0.006% by weight), and optional dipotassium hydrogenphosphate (0.01 to 0.05% by weight).

To prepare the oral compositions in solid form (such as tablets and troches), the sialogogue may be combined with nontoxic filler, binder, disintegrator, lubricant, surfactant, sweetener, and flavor (the last three mentioned above).

The filler is exemplified by cellulose and its derivatives, starch and its derivatives, sugars, and sugar alcohol. Their specific examples include crystalline cellulose, lactose, white soft sugar, mannitol, corn starch, potato starch, hyroxypropylstarch, calcium silicate, calcium hydrogenephosphate anhydride, and magnesium aluminometasilicate.

The binder is exemplified by hydroxypropyl cellulose, hydroxypropylmethyl cellulose, methyl cellulose, polyvinyl alcohol, polyvinylpyrrolidone, gelatin, dextrin, starch, and alpha starch.

The disintegrator is exemplified by carmellose, carmellose calcium, croscarmellose sodium, low substituted hydroxypropylcellulose, low substituted sodium carboxymethyl starch, and crospovidone.

The lubricant is exemplified by magnesium stearate, calcium stearate, sucrose ester of fatty acid, anhydrous silicic acid, light anhydrous silicic acid, and sodium stearyl fumarate.

The amount of the filler should be 1 to 10% by weight, particularly 3 to 5% by weight. The amount of the binder should be 0.1 to 1% by weight, particularly 0.2 to 0.3% by weight.

The food product may be formed from different materials according to its kind. For example, chewing gum may contain 10 to 50% by weight of saccharide (such as sugar) and 50 to 90% by weight of gum base, and candy may contain 35 to 40% by weight of starch syrup and 60 to 65% by weight of sugar.

EXAMPLES

The invention will be described below in more detail with reference to Experiment Examples, Working Examples, and Comparative Examples, which are not intended to restrict the scope thereof. In the following examples, "%" means "% by weight" unless otherwise mentioned. Also, in the following examples, weight average molecular weight (Mw) is represented by the one which is measured by GPC method.

GPC Method

A sample (2 mg) of polyglutamic acid is dissolved in 2 mL of 0.1 mol/L phosphate buffer solution (approximately pH 7.0). Each sample (2 mg) of pullulan P-82, pullulan P-10, pullulan P-50, pullulan P-200, and pullulan P-1600 is dissolved in 2 mL of 0.1 mol/L phosphate buffer solution to give standard solutions. The sample solution and the standard solution (each 50 μL) undergo GPC test, and the peak top molecular weight is obtained by using C-R7A•GPC program (product of SHIMADZU CORPORATION). The thus obtained value is regarded as the molecular weight.

<Conditions of analysis>

Detector: differential refractometer
Precolumn: Shodex Asahipak GS-IG 7B (product of Showa Denko K.K), 7.6 mm ID×100 mm (or equivalent)
Main column: Shodex Asahipak GF-710 HQ (product of Showa Denko K.K), 7.6 mm ID×300 mm+Shodex Asahipak GF-510 HQ (product of Showa Denko K.K), 7.6 mm ID×300 mm (or equivalent)
Column temperature: constant at about 40° C.
Mobile phase: 0.1 mol/L phosphate buffer solution (prepared by dissolving 7.1 g of disodium hydrogenphosphate anhydride ($Na_2HPO_4$) and 6.8 g of potassium dihydrogenphosphate ($KH_2PO_4$) in water just enough to make one liter.)
Flow-rate: 0.5 mL/min
Measurement time: 60 minutes.

Experiment Example 1

To Evaluate the Effect of Promoting Salivary Secretion

A sample of mouthwash was prepared from an aqueous solution containing 0.1% each of γ-polyglutamate and sodium hyaluronate. This sample was tested for the effect of promoting salivary secretion in the following manner.

Test for Promotion of Salivary Secretion:

Three panelists, who were made to feel thirsty by heavy exercise in the previous day, were tested for saliva secretion by the following steps which followed one after another.
(1) Mouth washing for 30 seconds with 20 mL of physiological saline.
(2) Spitting of saliva into a sputum mug, and measurement of the cumulative amount of saliva (for 30 minutes) at intervals of five minutes.
(3) Mouth washing for 30 seconds with 20 mL of the sample solution.
(4) Measurement of the cumulative amount of saliva (for 30 minutes) in the same way as in (2).

Figure 2:
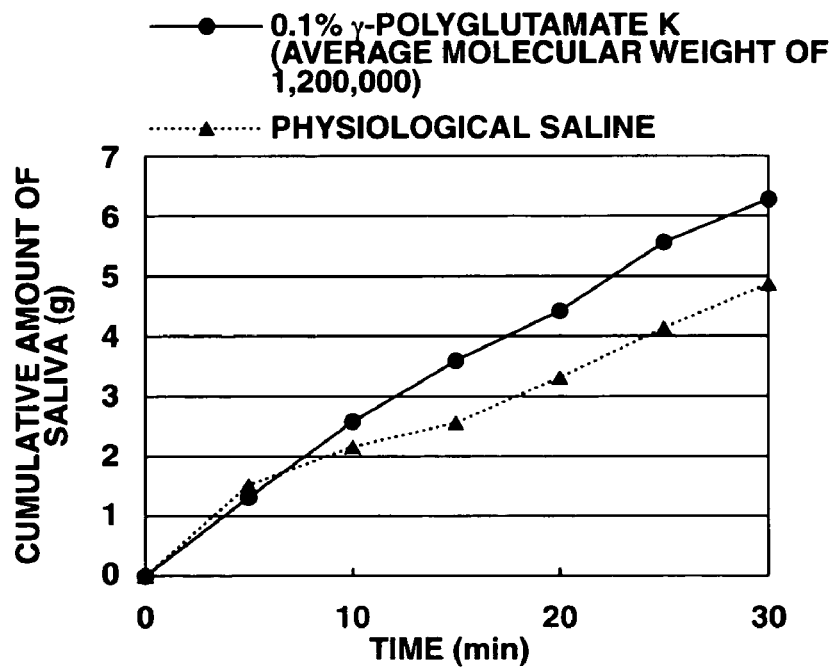
FIG. 2 is a graph showing how the cumulative amount of saliva changes with time after administration of potassium γ-polyglutamate (with an average molecular weight of 1,200,000) in Experiment Example 1.
Figure 3:
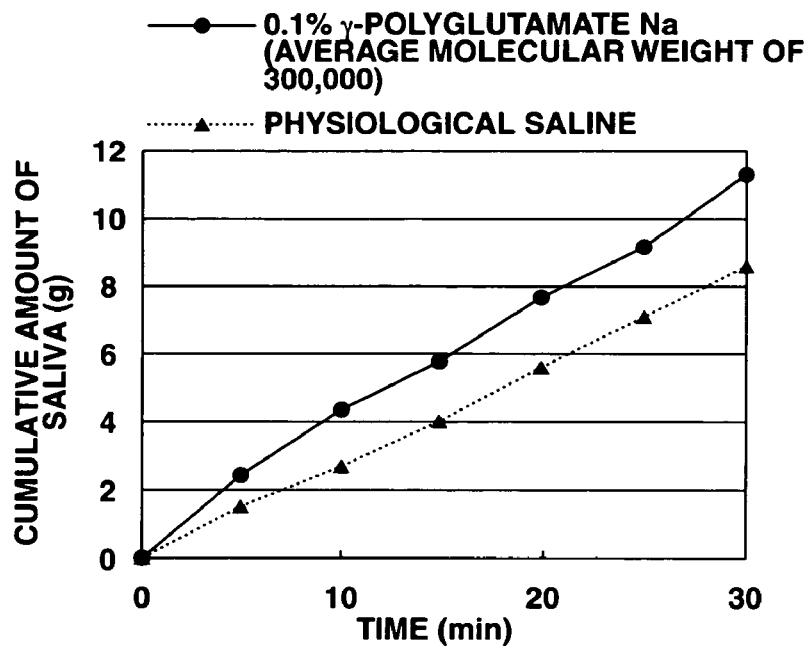
FIG. 3 is a graph showing how the cumulative amount of saliva changes with time after administration of sodium γ-polyglutamate (with an average molecular weight of 300,000) in Experiment Example 1.
Figure 4:
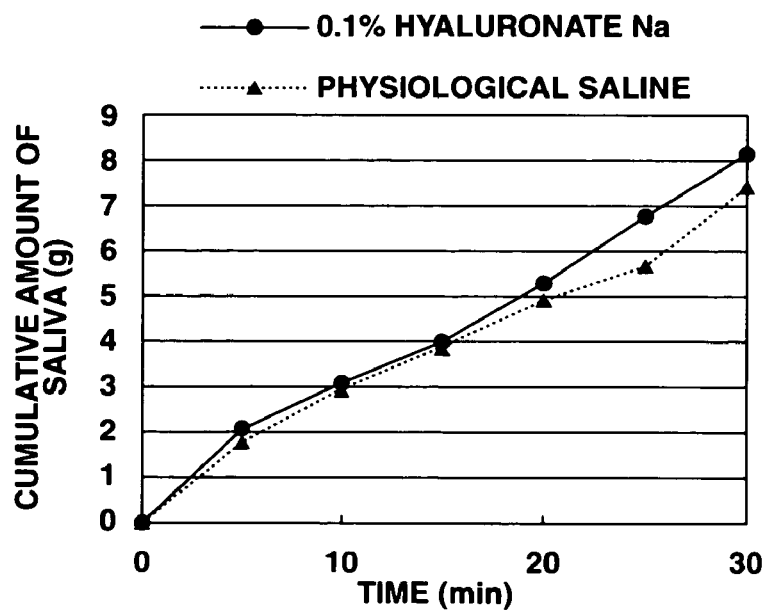
FIG. 4 is a graph showing how the cumulative amount of saliva changes with time after administration of sodium hyaluronate in Experiment Example 1.

Table 1 shows an increase (on average) from salivary secretion after mouth washing with physiological saline to salivary secretion after mouth washing with the sample solution. FIGS. 1 to 4 show the cumulative amount of saliva measured at intervals of five minutes.

TABLE 1

| Mouthwash solution | Ratio of increase in saliva secretion (%) |
|---|---|
| 0.1% sodium γ-polyglutamate (Mw = 1,200,000) | 151 |
| 0.1% potassium γ-polyglutamate (Mw = 1,200,000) | 128 |
| 0.1% sodium γ-polyglutamate (Mw = 300,000) | 132 |
| 0.1% sodium hyaluronate (for comparison) | 109 |

It is apparent from Table 1 and FIGS. 1 to 4 that γ-polyglutamic acid promotes salivary secretion.

Experiment Example 2

To Evaluate the Wet Feeling and Taste

Samples (0.1% aqueous solutions shown in Table 2) were prepared as shown in Table 2. Three panelists washed their mouth for 30 seconds with 20 mL of each sample solution and then spitted it out. Fifteen minutes later, the panelists rated the oral wet feeling and refreshed feeling according to the following criterion. Table 2 shows the results of rating (total points given by the three panelists).

TABLE 2

| Samples | Wet feel | Taste | Feature of taste |
|---|---|---|---|
| Sodium γ-polyglutamate (Mw = 1,200,000) | ◎ | ○ | Tasteless |
| Potassium γ-polyglutamate (Mw = 1,200,000) | ◎ | ○ | Tasteless |
| Sodium γ-polyglutamate (Mw = 300,000) | ◎ | ○ | Tasteless |
| Citric acid (for comparison) | X | X | Acidic |
| Cola nuts: water extract (for comparison) | X | Δ | Slightly spicy |
| Capparis masaikai seeds: 50% ethanol extract (for comparison) | X | X | Bitter sweet |
| Sodium hyaluronate (for comparison) | ○ | ○ | Tasteless |

*The γ-polyglutamic acid is the same one as used in Experiment Example 1.

Rating of Wet Feel

Standard for Rating:

| | Degree | | | |
|---|---|---|---|---|
| | Strong | Weak | Slight | None |
| Point | 3 | 2 | 1 | 0 |

Rating:

| | Total points | | | |
|---|---|---|---|---|
| | 7 to 9 | 4 to 6 | 1 to 3 | 0 |
| Degree | Strong | Weak | Slight | None |
| Rating | ◎ | ○ | Δ | X |

Rating of Taste

| | Degree | | |
|---|---|---|---|
| | None | Weak | Strong |
| Rating | ○ | Δ | X |

Examples 1 to 18 that follow show the formulations. Incidentally, the polyglutamate has a degree of neutralization at pH 7. A good effect of promoting salivary secretion was produced by all the samples of oral compositions and food products.

Example 1

Toothpaste

| | |
|---|---|
| Precipitated silica | 25.00% |
| Glycerin | 25.00 |
| Sorbit | 15.00 |
| Xylitol | 10.00 |
| Lauroyl decaglycerin ester | 1.00 |
| Myristic acid diethanolamide | 2.00 |
| Flavor | 1.00 |
| Saccharin sodium | 0.20 |
| Calcium γ-polyglutamate (Mw = 1,000,000) | 0.10 |
| Purified water | balance |
| Total | 100.0% |

Example 2

Liquid Dentifrice

| | |
|---|---|
| Aluminum hydroxide | 25.00% |
| Glycerin | 40.00 |
| Sorbit | 15.00 |
| Carboxymethyl cellulose (DP = 500) | 0.20 |
| Propylene glycol | 2.00 |
| Sodium laurate | 1.50 |
| Decaglyceryl monolaurate | 1.00 |
| Flavor | 1.00 |
| Saccharin sodium | 0.10 |
| Sodium γ-polyglutamate (MW = 1,500,000) | 0.10 |
| Purified water | balance |
| Total | 100.0% |

Example 3

Oral Ointment

| | |
|---|---|
| Liquid paraffin | 15.00% |
| Cetanol | 10.00 |
| Glycerin | 20.00 |
| Polyoxyethylene sorbitan fatty acid ester | 5.00 |
| Flavor | 0.50 |
| Saccharin sodium | 0.10 |
| Lysine γ-polyglutamate (Mw = 300,000) | 0.20 |
| Purified water | balance |
| Total | 100.0% |

Example 4

Mouthwash

| | |
|---|---|
| Ethanol | 20.00% |
| Flavor | 1.00 |
| Polyoxyethylene (EO 60) hydrogenated castor oil | 0.30 |
| Sodium monofluorophosphate | 0.10 |
| Saccharin sodium | 0.05 |
| Sodium γ-polyglutaxnate (Mw = 1,200,000) | 0.20 |
| Purified water | balance |
| Total | 100.0% |

Example 5

Gargle Tablet

| | |
|---|---|
| Sodium bicarbonate | 53.0% |
| Citric acid | 18.0 |
| Anhydrous sodium sulfate | 12.0 |
| Dibasic sodium phosphate | 10.0 |
| Polyethylene glycol | 3.0 |
| Flavor | 2.0 |
| Ammonium γ-polyglutamate (Mw = 80,000) | 2.0 |
| Total | 100.0% |

Example 6

Troche

| | |
|---|---|
| Xylitol | 92.0% |
| Gum acasia | 5.0 |
| Talc | 2.0 |
| Magnesium stearate | 0.7 |
| Potassium γ-polyglutamate (Mw = 1,200,000) | 0.3 |
| Total | 100.0% |

Example 7

Chewing Tablet

| | |
|---|---|
| Erythritol | 85.0% |
| Potato starch | 4.0 |
| Talc | 3.5 |
| Magnesium stearate | 1.5 |
| Citric acid | 5.0 |
| Arginine γ-polyglutamate (Mw = 1,200,000) | 1.0 |
| Total | 100.0% |

Example 8

Denture Stabilizer (in Gum Form)

| | |
|---|---|
| Vinyl acetate resin | 60.0% |
| Light calcium carbonate | 3.0 |
| Yellow beeswax | 3.0 |
| Polypropylene glycol | 3.0 |
| Ethanolamine γ-polyglutamate (Mw = 1,500,000) | 1.0 |
| 60% ethanol | balance |
| Total | 100.0% |

Example 9

Denture Stabilizer (in Powder Form)

| | |
|---|---|
| Sodium carboxymethyl cellulose | 74.0% |
| Polyethylene oxide | 24.0 |
| γ-polyglutamic acid (Mw = 300,000) | 2.0 |
| Total | 100.0% |

Example 10

Denture Stabilizer (in Paste Form)

| | |
|---|---|
| Sodium carboxymethyl cellulose | 32.0% |
| Polyethylene oxide | 13.0 |
| Vaseline | 40.0 |
| Arginine γ-polyglutamate (Mw = 1,000,000) | 1.0 |
| pH adjustor | 0.2 |
| Flavor | 0.1 |
| Antiseptics | q.s. |
| Coloring matter | q.s. |
| Liquid paraffin | balance |
| Total | 100.0% |

Example 11

Mouth Refrigerant

| | |
|---|---|
| Ethanol | 30.0% |
| Xylitol | 10.0 |
| Flavor | 2.0 |
| Polyoxyethylene (EQ 60) hydrogenated castor oil | 1.5 |
| Potassium γ-polyglutamate (Mw = 1,000,000) | 1.0 |
| Purified water | balance |
| Total | 100.0% |

Example 12

Solution for the Oral Care System with Water-Supply and Suction Functions

| | |
|---|---|
| Glycerin | 2.0% |
| Xylitol | 2.0 |
| Polyoxyethylene (EQ 60) hydrogenated castor oil | 1.0 |
| Ethanolamine γ-polyglutamate (Mw = 1,200,000) | 0.5 |
| pH adjustor | 0.2 |
| Flavor | 0.2 |
| Antiseptics | q.s. |
| Coloring matter | q.s. |
| Purified water | balance |
| Total | 100.0% |

Example 13

Artificial Saliva

| | |
|---|---|
| Potassium chloride | 0.15% |
| Sodium chloride | 0.06 |
| Magnesium chloride | 0.005 |
| Calcium chloride | 0.015 |
| Hydroxypropyl cellulose | 0.1 |
| Glycerin | 1.0 |
| Calcium γ-polyglutamate (Mw = 1,500,000) | 0.5 |
| Flavor | 0.02 |
| Antiseptics | q.s. |
| Purified water | balance |
| Total | 100.0% |

Example 14

Swallowing Assistant (4.5 g for 100 mL Water)

| | |
|---|---|
| Xanthan gum | 20.0% |
| Guar gum | 4.0 |
| Ammonium γ-polyglutamate (Mw = 300,000) | 1.0 |
| Dextrin | balance |
| Total | 100.0% |

Example 15

Candy

| | |
|---|---|
| Sugar | 50.0% |
| Starch syrup | 33.0 |
| Organic acid | 2.0 |
| Flavor | 0.2 |
| Sodium γ-polyglutamate (Mw = 300,000) | 0.1 |
| Purified water | balance |
| Total | 100.0% |

Example 16

Chewing Gum

| | |
|---|---|
| Sugar | 53.4% |
| Gum base | 20.0 |
| Glucose | 10.0 |
| Starch syrup | 16.0 |
| Flavor | 0.5 |
| γ-polyglutamic acid (Mw = 80,000) | 0.1 |
| Total | 100.0% |

Example 17

Drinks

| | |
|---|---|
| Glucose | 1.35% |
| Fructose | 1.35 |
| Milk component | 0.1 |
| Sodium γ-polyglutamate (Mw = 80,000) | 0.1 |
| Sodium chloride | 0.029 |
| Vitamin C | 0.03 |
| Vitamin B1 | 0.00022 |
| Valine | 0.0384 |
| Leucine | 0.0462 |
| Isoleucine | 0.0154 |
| Citric acid | 0.01 |
| Malic acid | 0.01 |
| Flavor | 0.01 |
| Water | balance |
| Total | 100.0% |

Example 18

Gummi

| | |
|---|---|
| Sugar | 40.2% |
| Starch syrup | 48.2 |
| Gelatin | 8.0 |
| Fruit juice | 2.0 |
| Citric acid | 0.5 |
| Malic acid | 0.5 |
| Flavor | 0.5 |
| Calcium γ-polyglutamate (Mw = 300,000) | 0.1 |
| Total | 100.0% |

The invention claimed is:

1. A method of treating xerostomia, said method comprising:
   administering a sialogogue composition comprising polyglutamic acid having an average molecular weight of 10,000 to 5,000,000 Daltons or a salt thereof selected from the group consisting of sodium salt, potassium salt, magnesium salt, calcium salt, ammonium salt, ethanolamine salt, and basic amino acid salt as a sialogogue; and
   a carrier to form a product selected from the group consisting of chewing gum, a swallowing assistant, candy, drinks, and gummi to a patient in need thereof.

2. A method of treating xerostomia, said method comprising:
   administering an oral composition comprising polyglutamic acid having an average molecular weight of 10,000 to 5,000,000 Daltons or a salt thereof selected from the group consisting of sodium salt, potassium salt, magnesium salt, calcium salt, ammonium salt, ethanolamine salt, and basic amino acid salt as a sialogogue; and
   a carrier to form a product selected from the group consisting of toothpaste, mouthwash, chewing tablet, oral ointment, gargling tablet, troches, artificial saliva, denture stabilizer, and solution for the oral care system with water supply and suction functions to a patient in need thereof.

3. The method of claim 1, wherein the amount of polyglutamic acid or a salt thereof is 0.001 to 10% by weight of the total composition.

4. The method of claim 2, wherein the amount of polyglutamic acid or a salt thereof is 0.001 to 10% by weight of the total composition.

5. The method of claim 1, wherein the sialogogue composition is administered 1 to 6 times a day.

6. The method of claim 2, wherein the oral composition is administered 1 to 6 times a day.

7. The method of claim 1, wherein said polyglutamic acid or a salt thereof is the sole active ingredient.

8. The method of claim 2, wherein said polyglutamic acid or a salt thereof is the sole active ingredient.

9. A method of treating xerostomia, said method comprising:
   administering an oral composition comprising polyglutamic acid having an average molecular weight of 10,000 to 5,000,000 Daltons or a salt thereof selected from the group consisting of sodium salt, potassium salt, magnesium salt, calcium salt, ammonium salt, ethanolamine salt, and basic amino acid salt as a sialogogue.

10. The method of claim 1 wherein said polyglutamic acid is a γ-polyglutamic acid.

* * * * *